United States Patent [19]

Withers et al.

[11] Patent Number: 5,167,193
[45] Date of Patent: Dec. 1, 1992

[54] MEDICAL WASTES DISPOSAL SYSTEM
[75] Inventors: L. Andrew Withers, Atlanta; David W. Hughes, Chamblee, both of Ga.
[73] Assignee: McDonald, Withers & Hughes, Inc., Atlanta, Ga.
[21] Appl. No.: 699,915
[22] Filed: May 14, 1991
[51] Int. Cl.$^5$ .............................................. F23G 5/00
[52] U.S. Cl. ........................ 110/346; 110/242; 110/246; 206/63.5; 206/366; 206/570
[58] Field of Search ............... 110/235, 237, 246, 346, 110/242; 206/63.5, 366, 570

[56] References Cited

U.S. PATENT DOCUMENTS

| | | |
|---|---|---|
| 746,815 | 12/1903 | Ghiradelli . |
| 1,607,923 | 11/1926 | Sebell . |
| 1,643,252 | 9/1927 | McCrery . |
| 3,072,512 | 1/1963 | Gaylord . |
| 3,086,674 | 4/1963 | Scheuerman ................ 156/83 |
| 3,292,776 | 12/1966 | Penn ........................ 206/43 |
| 3,543,996 | 12/1970 | West ........................ 220/24 |
| 3,637,072 | 1/1972 | Narusawa et al. ............ 229/43 |
| 4,328,904 | 5/1982 | Iverson ..................... 220/256 |
| 4,351,434 | 9/1982 | Elisha ...................... 206/366 |
| 4,375,849 | 3/1983 | Hanifi ...................... 206/366 |
| 4,454,944 | 6/1984 | Shillington et al. .......... 206/366 |
| 4,485,918 | 12/1984 | Mayer ...................... 206/366 |
| 4,494,652 | 1/1985 | Nelson ..................... 206/366 |
| 4,520,926 | 6/1985 | Nelson ..................... 206/366 |
| 4,657,138 | 4/1987 | Watson ..................... 206/366 |
| 4,736,844 | 4/1988 | Scott et al. ................ 206/370 |
| 4,767,008 | 8/1988 | Warnecke et al. ............ 206/570 |
| 4,779,728 | 10/1988 | Hanifl et al. ............... 206/366 |
| 4,807,752 | 2/1989 | Chodorow ................... 206/63.5 |
| 4,808,286 | 2/1989 | Angelo ..................... 110/246 |
| 4,816,307 | 3/1989 | Honeycutt .................. 428/34.1 |
| 4,828,107 | 5/1989 | Spencer .................... 206/366 |
| 4,842,138 | 6/1989 | Sandel et al. .............. 206/370 |
| 4,848,570 | 7/1989 | Gosciniak .................. 206/366 |
| 4,848,587 | 7/1989 | Nipp ....................... 206/571 |
| 4,850,290 | 7/1989 | Benoit et al. .............. 110/246 |
| 4,936,449 | 6/1990 | Conrad et al. .............. 206/366 |
| 4,969,554 | 11/1990 | Sawaya ..................... 206/370 |
| 4,972,950 | 11/1990 | Shillington ................ 206/366 |
| 4,984,686 | 1/1991 | Shillington ................ 206/366 |
| 5,020,665 | 6/1991 | Bruno ...................... 206/366 |
| 5,024,326 | 6/1991 | Sandel et al. .............. 206/366 |
| 5,040,972 | 8/1991 | Kleinhenz et al. ........... 110/242 |
| 5,086,716 | 2/1982 | Lafser, Jr. ................ 110/346 |

FOREIGN PATENT DOCUMENTS

2040268  1/1980  United Kingdom .

OTHER PUBLICATIONS

Syd Syringe and Needle Disposers (leaflet) Bemis Health Care.
Syd Large Volume Diohazard Disposer (leaflet) Bemis Health Care.
Sharpsafe Bio-Hazardous Waste Containment System (2 leaf brochure) by Concord Labatories, Inc.
Terminal Keepers for Sharps and Broken Glass (leaflet) by Whitney Products, Inc.
Sharpsafe Directions for Assembly and Disposal (leaflet) by Concord/Portex, A Smiths Industries Medical Systems Company.
Terminal Laboratory Deoderant (leaflet) by Whitney Products, Inc.
Terminal Biohazard System for Laboratory, Hospital & Clinic (leaflet) by Whitney Products, Inc.
pp. 32, 33 & 47 of Pigalog (catalog) by New Pig Corporation.
The Microban Effect in Health Care Products Inherent Protection Against Hospital Cross-Contamination (leaflet) by Mcroban Products Co. 1983.

*Primary Examiner*—Henry C. Yuen
*Attorney, Agent, or Firm*—Hopkins & Thomas

[57] ABSTRACT

The system (10) for collecting and disposing of medical sharps and other medical wastes includes a housing (11) and its telescopic cover (9) which are fabricated of biodegradable and combustible material such as natural cellulose, non-natural cellulose, and other materials and an absorbent biodegradable and combustible absorption package (30) or insert (35) can be placed in the bottom of the holding chamber (12) for absorbing any liquids emitted from the sharps and other medical wastes, and for enhancing the combustion of the medical sharps and other medical wastes when the housing is placed in a furnace. The system for collecting and disposing of medical wastes when burned, evolves no more than trace levels of sulfur or chlorine and yields substantially only biodegradable ash.

34 Claims, 3 Drawing Sheets

MEDICAL WASTES DISPOSAL SYSTEM

FIELD OF THE INVENTION

The present invention relates in general to a system for disposing of medical wastes. More particularly, the invention relates to a system for collecting and disposing of medical sharps and other medical wastes.

BACKGROUND OF THE INVENTION

The term "medical sharps" generally is defined as medical instruments having a sharp cutting edge or a sharp point. In the medical environment, sharps comprise hypodermic needles, syringes, scalpel blades, and the like. Other medical wastes, including chemotherapy and pathological wastes comprise surgical tubing, washcloths, surgical gloves, cultures of infectious agents, and the like. After use, medical sharps and other medical wastes must be safely collected and disposed of without creating a hazard for the hospital personnel, patients, or maintenance personnel.

Presently, the hospital protocol is to use and immediately dispose of these medical wastes in receptacles, such as plastic, wall-mounted receptacles or in large receptors having an open top wall, otherwise known as "kick buckets". Typically the receptacles are placed in strategic locations throughout the hospital or other medical treatment facility, such as on the wall in the patient's rooms, in the hall outside the patient's room, in treatment rooms, operating rooms, and emergency rooms so as to be available for receiving the medical wastes immediately and conveniently after use by the nurse, physician, or other medical personnel. Additionally, the kick buckets are generally placed in operating rooms and emergency rooms for receiving large volumes of various types of medical wastes from authorized medical personnel only. The receptacles must be suitably sized and shaped to receive the anticipated amount of medical waste over a period of time, depending on the protocol of the medical facility, and the receptacles must easily receive yet securely and safely retain the medical waste so as to avoid presenting a hazard to children or to disoriented patients or to curious visitors.

After these receptacles are filled with medical wastes they are collected for disposal, usually for burning in an incinerator. The collection procedure usually requires relatively unskilled personnel to move about the hospital with a plastic bag or other relatively large container and to place the filled receptacles in the bag, and to replace the used receptacles with new empty receptacles, for example by dismounting the used plastic receptacles from their wall brackets and mounting the new receptacles in the wall brackets. After replacement and collection of the medical waste receptacles, the collected receptacles are securely packaged in a larger container such as a plastic bag or cardboard box and the bag or box is carried to a burn facility.

During the containment and collection procedure of the medical wastes, there is the hazard that the medical waste materials will contaminate the personnel who are handling or are exposed to the wastes. Experience demonstrates that accidents caused by the medical waste materials through skin scratch or puncture and other exposure are occasional causes of injury to personnel and such accidents are a considerable expense to hospitals and insurance companies.

For example, when the used receptacles that are filled with medical wastes are being removed from their holders or being transported, the needle of a syringe can protrude from or escape from its individual receptacle and scratch or puncture the personnel handling the receptacle.

Therefore, it is highly desirable that the use-and-dispose method provides for safe containment and collection of the medical sharps and other wastes within the hospital environment by providing a collector which is puncture resistant and leak resistant.

Another problem can be created during disposal of the medical wastes. The usual method of disposal is incineration, whereby the medical wastes are converted into ash for delivery to a landfill, etc. The disposal systems for the medical wastes range from on-site incinerators to contract disposal services which transport the medical wastes to off-site burn facilities. Generally, the treatment plants incinerate the collectors and the medical wastes contained in the collectors and then bury the residue of the burned medical wastes and collectors in a landfill. Most of the known prior art medical waste disposal collectors are composed of plastics and when incinerated can yield a partially pyrolized plastic residue, which is essentially a tar ash. This type of ash is non-biodegradable.

An incineration technique is especially advantageous for disintegrating contaminated sharps and other pathological wastes, because incineration has the ability to convert the contaminated substances into a noncontaminated ash. However, when certain materials such as plastics of a syringe are burned, ashes from the incineration of these materials can become a tar ash or residue which when buried in a landfill, is non-biodegradable waste. Although the ashes of plastic syringes and some other types of plastic wastes will be delivered to landfills, it is highly desirable to avoid the use of plastic collectors for these wastes, because when plastic collectors are burned they can emit toxic gases to the atmosphere and create even more non-biodegradable ash, which is an undesirable additive to a landfill.

Thus, it would be advantageous to provide a disposable collector system for collecting and disposing of medical sharps and other medical wastes that is safe and efficient, biodegradable, and is simple to handle, and which can be incinerated without the evolution of any substantial toxic gases and which when burned aids in rendering the wastes. It also would be desirable to fabricate the collector of a combustible material that yields substantially only biodegradable ash upon incineration and to adjust the mass of the collector with respect to the anticipated mass of the collected wastes so as to control the ratio of the resulting biodegradable ash of the collector with respect to the non-biodegradable ash of the waste, when burned.

SUMMARY OF THE INVENTION

Briefly described, the present invention comprises a system for collecting and disposing of medical sharps and other medical wastes, which provides a leak resistant, combustible, and biodegradable housing including a closed lower portion and an upper portion with an opening for receiving medical wastes. In one embodiment of the invention the upper portion of the housing includes a lid or an openable area such as a scored portion of the housing for yieldably opening the upper portion of the housing while normally maintaining the housing closed, and a wall bracket is provided for mounting the housing to a wall for releasably holding the wall of the housing in a firm and safe condition.

Additionally, the collector housing will be formed of a renewable resource or non petroleum-based material, which when incinerated will yield substantially only a biodegradable ash, otherwise known as mineral-ash. In a preferred embodiment of the invention, the entire housing will be fabricated of material possessing combustible and biodegradable characteristics. When incinerated in a furnace environment the collector initially retains its medical wastes and the heat of combustion of the collector adds to the heat used to render the medical wastes in the collector.

In another preferred embodiment of the invention, a wall-mounted head or lid releasably supports the disposable collector housing, and the wall mounted lid of the housing receives and passes the medical wastes into its collector housing. This head is formed of a clear material such as glass or any other material with glass-like qualities wherein the user can view inside the housing as the medical wastes are collected and fill up the housing. Additionally, the head will be cleanable and non-stainable.

The present invention also provides an absorbent material located inside a collector housing for absorbing any fluid emitted from or residual on the discarded medical wastes. A preferred form of the absorbent material possesses all or a combination of absorbent, cellulosic, antimicrobial, antibacterial, antifungal, biodegradable, and combustible properties, whereby any residual fluid inside the collector housing tends to be preferentially absorbed and dispersed in the absorbent material to protect personnel from coming in direct contact with the liquid medical wastes, and when incinerated, the dispersion of the fluids in the absorbent material tends to enhance combustion of the absorbed liquid medical wastes.

In another embodiment of this invention the housing will comprise a dual-wall construction, wherein the material of the housing also will be fabricated of a combustible and biodegradable material. In addition, this embodiment will provide an effective approach to controlling the wall thickness of the housing, which will substantially increase the puncture-resistance factor of the housing. The general dual-wall construction can be combined with an absorptive package or insert within the housing to further improve the leak resistance of the system for collecting and disposing of medical wastes.

It is therefore an object of the present invention to provide an apparatus which collects, contains, and disposes of medical wastes in a safe, convenient, and inexpensive manner.

Another object of the present invention is to provide a collector housing which is combustible and biodegradable and formed from a renewable resource, otherwise known as a non petroleum-based material.

A further object of the present invention is to provide such a system for collecting and disposing of medical sharps, whereby the housing itself is puncture resistant, leak resistant, rigid, and combustible for safe containment and effective treatment of medical sharps.

It is yet another object of the present invention to provide a collector housing for collecting and disposing of medical wastes in a safe and economical manner, and to provide within the housing an absorptive, antimicrobial, antifungal, antibacterial material whereby when wastes are deposited into the housing, any fluid emitted from the wastes will be absorbed and disinfected.

A further object of this invention is to provide a collector housing for collecting and disposing of medical waste wherein an absorbent and combustible material is contained within the housing adjacent the space where the medical wastes are collected.

Another object of this invention is to provide a system for collecting and disposing of medical wastes, such as syringes used for injecting medication, whereby the system comprises a combustible housing that, upon combustion, fully renders the medical waste within the environment of a furnace.

It is another object of the present invention to provide such a system of collecting and disposing of medical wastes wherein the housing for collecting the medical wastes is of appropriate mass and rigidity during initial burning to substantially retain the medical wastes therein, until the wastes combust and begin to be reduced to ash.

Another object of the present invention is to provide such a collector system in which the housing itself comprises a combustible material that, upon combustion leaves substantially only biodegradable ash.

A further object of the present invention is to provide a system for collecting and disposing of medical wastes wherein the entire housing is fabricated of a clean burning combustible material that, upon combustion, emits gases which are substantially free of sulfur or chlorine.

A more complete understanding of the present invention will be had by those skilled in the art, as well as an appreciation of additional advantages, which will become apparent upon reading the detailed description of the preferred embodiment and examining the drawings, the following of which is a brief description.

DETAILED DESCRIPTION

Figure 1:
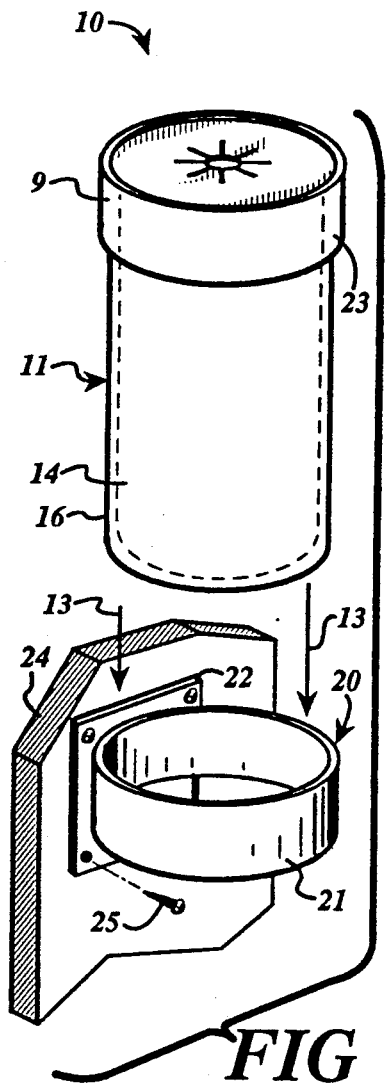
FIG. 1 is an exploded perspective view of the system for collecting and disposing of medical wastes and its wall holder.
Figure 2:
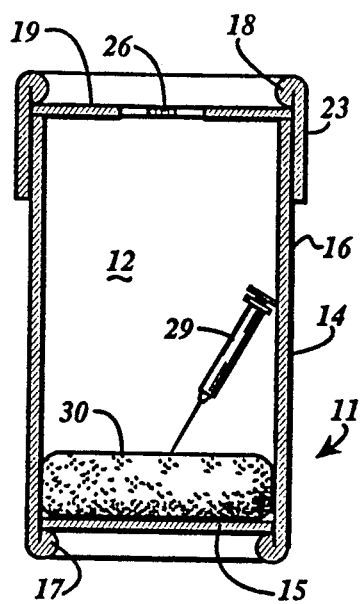
FIG. 2 is a side cross-sectional view of the system for collecting and disposing of medical wastes of FIG. 1, showing a syringe that has been deposited in the collector housing.
Figure 3:
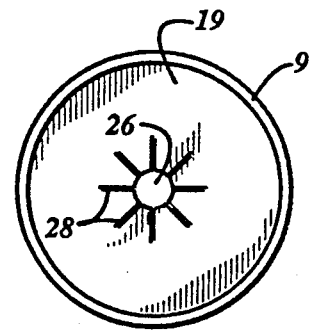
FIG. 3 is a top view of the circular lid of the system for collecting and disposing of medical wastes of FIG. 1.

Referring now in more detail to the drawings, in which like numerals indicate like parts throughout the several views, FIGS. 1-3 illustrate the system 10 for collecting and disposing of medical wastes which includes a cylindrical housing 11 and its wall mount 20, according to the present invention. The housing 11 is shown separated from a wall mount 20 and ready for insertion into a circular sleeve 21 of the wall mount 20 as indicated by the downward directional arrows 13. The wall mount 20 comprises a mounting bracket 22, preferably attached to a wall 24 by multiple screws 25 which extend through openings of the bracket into the wall of the building structure, and the mounting bracket 22 supports the circular sleeve 21 in an upright attitude.

The housing 11 comprises an upper telescoping cover 9 and a lower cylindrical body 14. The upper telescopic cover can be attached, such as by adhesive connection, to the cylindrical body of the housing which includes a cylindrical side wall 16 with the lower end portion of the side wall turned inwardly to form a circular flange or seat 17 (FIG. 2) and the bottom wall or "plug" 15 is positioned inside the side wall and is supported on the seat 17. Lower cylindrical body 14 and its bottom wall 15 define a holding chamber 12 which is open at its upper end. An absorption pack 30 resting on bottom wall 15 acts to absorb and disperse liquids throughout the absorption pack and can also be partially penetrated by syringe needles and other medical sharps. The configuration and density of the material of the insert provide preferential absorption and dispersion of the liquid medical wastes.

The telescoping cover 9 includes a cylindrical side wall 23 which is of sufficient internal breadth to telescopically fit over the upper end of the cylindrical side wall 16 of the lower cylindrical body 14 with a tight fit, and the telescoping cover 9 is of a diameter larger than the space defined by the sleeve 21 of the mounting bracket 22 so that when the housing 11 is moved down into the circular sleeve 21 of the wall mount 20 the cover 9 supports the cylindrical housing 11 in the mounting bracket. The telescoping cover 9 has on its uppermost portion, upper inwardly projecting circular seat 18 and a top wall or "plug" 19 defining a circular aperture 26, with score lines 28 radiating outwardly from the aperture which can separate when medical sharps or other medical wastes are thrust downwardly through the top wall.

The preferred embodiment of the cylindrical housing used for collecting and disposing of medical sharps and other medical waste will be formed of a leak resistant, rigid, combustible material selected from: cellulosic materials, such as paper stock, cardboard, wood, and particle board, non-natural cellulosic materials such as rayon, cellophane, and cellulose-nitrate, and other biodegradable materials such as natural rubber and natural wax, whereby when burned forms gases of combustion which yields no more than trace levels of sulfur or chlorine. The cylindrical housing can also be colored by color agents for designating medical sharps, medical wastes, or chemotherapy waste, whereby the coloring agents are also biodegradable. The housing material can include an anti-microbial additive such as a commercially available disinfectant. In addition, it is understood that a cylindrical housing as illustrated in the drawings is only one of many configurations the system for collecting and disposing of medical wastes can take. The housing can be of various sizes and proportions and can be of shapes such as rectangular, octagonal, etc.

FIG. 2 shows a used syringe 29 inserted through the aperture 26 and into the holding chamber 12. The aperture 26 formed in the top wall 19 is sized in accordance with the expected size of the medical waste items to be collected so that the medical sharp or other medical waste must slightly stretch the aperture along the score lines 28 when being inserted in the collector. This tight and yielding fit of the syringe avoids inadvertent escape of the syringe during subsequent removal and collection of the collector. The needle of the syringe which might hold contaminants, usually penetrates the absorption package 30. The absorption package is formed of a group of materials selected from: natural cellulosic, non-natural cellulosic, and other materials which are biodegradable and combustible, with antimicrobial additives, such as commercially available disinfectants. As shown in FIG. 2, this absorption package is placed in the lower portion of the cylindrical housing 11 abutting the bottom plug 15 and the cylindrical side wall 16.

Figure 4:
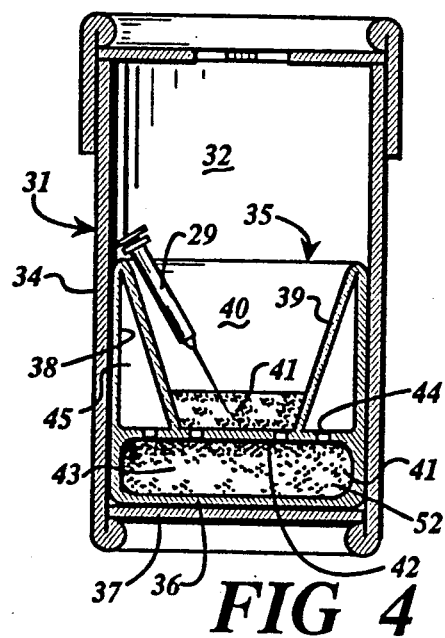
FIG. 4 is a side cross-sectional view of another embodiment and its insert.

FIG. 4 illustrates an additional embodiment of the absorption package of the invention, showing a housing 31 for collecting and disposing of medical sharps and with the absorption package comprising an insert 35. The insert fits snugly into the lower portion of the holding chamber 32 of the cylindrical body 34 with a bottom wall 36 of the insert 35 abutting the bottom wall 37 of the housing. The insert 35 has an annular outer vertical side wall 38 extending from the bottom wall 36 of the insert, upwards to a height less than or equal to the height of the cylindrical side wall 34. An inwardly and downwardly inclined conically shaped inner wall 39 extends downwardly from the upper edge of the vertical side wall 38 of the insert and intersects horizontal false bottom wall 42 to form a conically shaped receptacle 40, and an annular hollow cavity 45 surrounds the conically shaped receptacle. A cork 41 or other means for being partially penetrated by, and therefore, retaining medical sharps is positioned in the lower portion of the conically shaped receptacle 40. False bottom wall 42 forms lower chamber 43 above bottom wall 36, and absorptive and combustible material 52 is contained in the lower chamber. Thus, the conically shaped receptacle 40 tends to guide the medical wastes inwardly and downwardly toward the cork, etc. 41 in the lower portion of the conically shaped receptacle as the medical sharps and other medical wastes fall downwardly into the receptacle, whereby excess fluids of the wastes will be absorbed by and dispersed in the absorptive and combustible material 52. Multiple air holes 44 are defined in the false bottom wall 42, wherein any excess fluids can have access to the absorption material 52 in the lower chamber 43 to further absorb any fluids emitted from the medical sharps. The air holes 44 also serve as ventilators to enhance combustion within the holding chamber 32, when incinerated.

Figure 5:
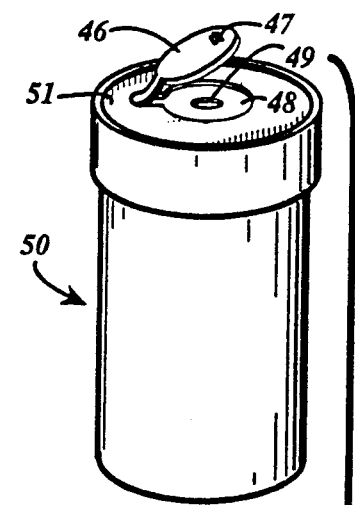
FIG. 5 is a perspective view of another embodiment of the invention having a modified lid structure.
Figure 5:
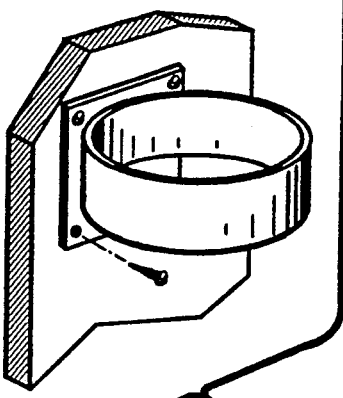

FIG. 5 illustrates an additional embodiment 50 of a receptor for medical sharps, wherein the aperture 49 of the top wall 51 is closed by a lid 46 having a tab 47 that can be grasped and pulled upwardly to reveal an inner recessed lip 48 about the aperture 49 for receiving medical waste.

Figure 6:
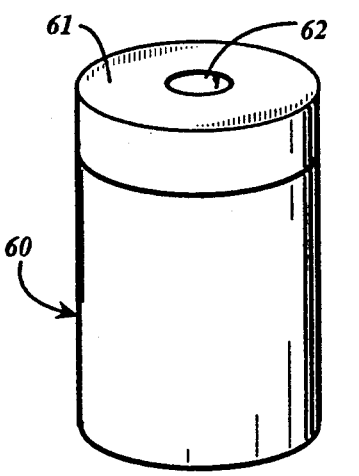
FIG. 6 is a perspective view of a third embodiment of the invention which is of a monolithic construction.
Figure 7:
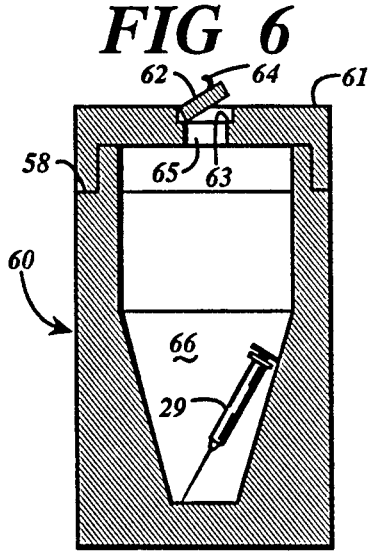
FIG. 7 is a side cross-sectional view of the embodiment of FIG. 6.

FIGS. 6 and 7 illustrate another embodiment 60 of the cylindrical housing 60 which is a monolithic structure. A top wall 61 defines an aperture 65 and a circular lid 62 closes the aperture, with the lid having a tab 64 for opening the circular lid. The circular lid 62 abuts an inner recessed flange 63 about the aperture 65.

The housing 60, which can be cylindrical on the outside as shown or other shapes, defines a holding chamber 66 for receiving medical wastes. The inside surfaces can be tapered for funneling the medical sharps 29 and other medical wastes toward a centrally located position, if desired. The housing 60 has a recessed upper annular rim 58 in the upper portion of its annular side wall for receiving an interlocking telescopic cover 61 to be mated with the rim 58 and forms a smooth exterior side wall of the housing.

Figure 8:
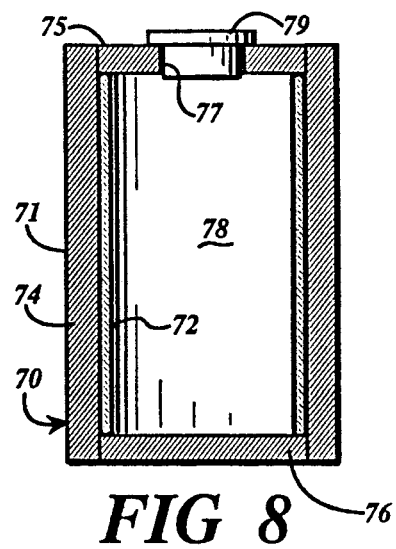
FIG. 8 is a side cross-sectional view of another embodiment, which includes a dual wall construction of the cylindrical housing.

FIG. 8 shows another embodiment 70 of the housing which includes a dual cylindrical sidewall structure 71 having an inner cylindrical side wall 72 and an outer concentric cylindrical side wall 74. The inner side wall 72 is shorter than outer side wall 74 and has its upper and lower ends offset inwardly of the ends of the outer side wall 74. A top wall 75 and a bottom wall 76 supplement the length of the inner side wall 72 at both ends to form smooth ends to the housing for collecting and disposing of medical wastes. A holding chamber 78 is defined by the inner side wall 72, and the top wall 75 and the bottom wall 76. It is understood that the inner side wall 72 and the outer side wall 74 may vary in wall thickness either singly or taken in combination with each other. The top wall 75 defines an aperture 77 and a plug 79 is inserted in and closes the aperture.

Figure 9:
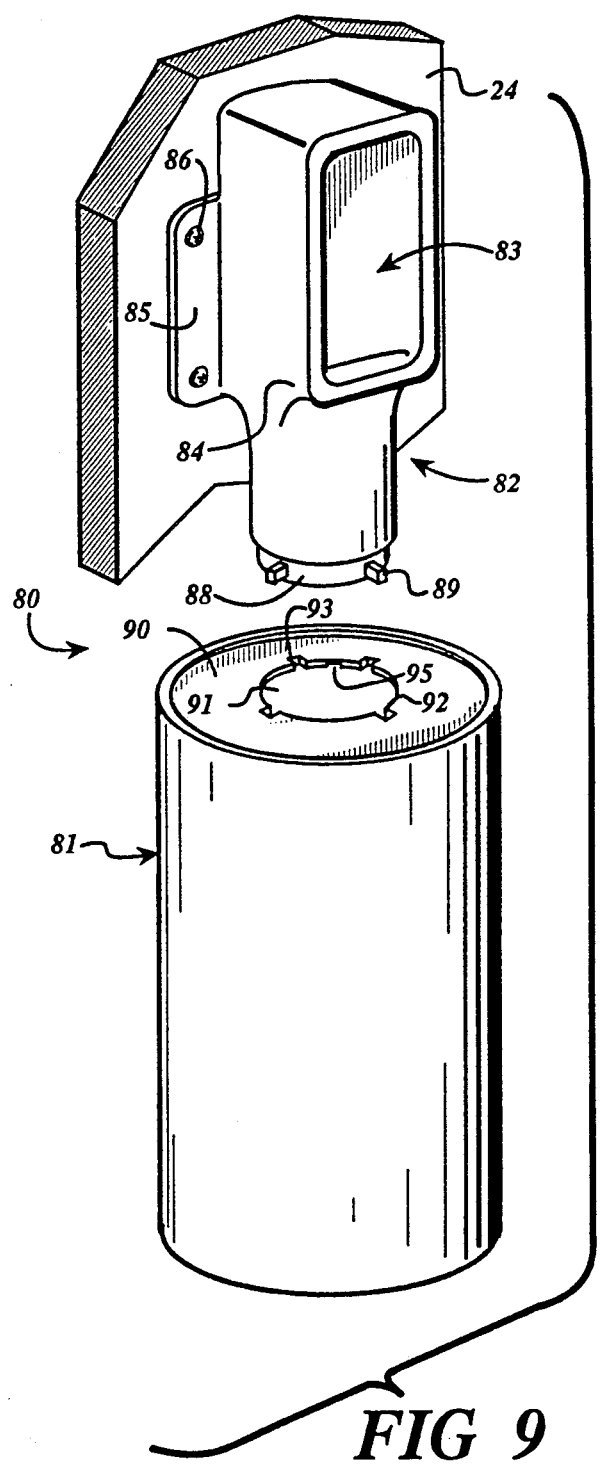
FIG. 9 is an exploded perspective view of yet another embodiment which includes a lid having a vertically oriented opening and a collector housing.

FIG. 9 shows another embodiment 80 of the system, having a head 82 mounted to the wall 24. The head 82 defines an elongated opening 83 and a curved chute 84 extending inwardly and downwardly from the opening toward the cylindrical housing 81 below, which receives the medical sharps. The head 82 has a flange 85 with screws 86 or other fasteners for securing the flange to a wall 24. The lower portion of the head 82 defines a cylindrical collar 88 with multiple protruding studs 89 extending outwardly therefrom for releasably locking together the head 82 and the cylindrical housing 81.

The cylindrical housing 81 includes a top wall 90 having an aperture 91. A rim 92 defines the aperture 91 and has open slots 93 formed therein for receiving the studs 89 of the collar 88 of the head 82 to pass through the top wall, and closed notches 95 to nonrotatably mount the housing on the head 82. Therefore, as medical personnel fill the cylindrical housing, they can see through the transparent or translucent head 82 and downwardly through the opening 83 to determine the volume of medical waste present in the housing 81 and replace the housing as necessary.

Figure 10:
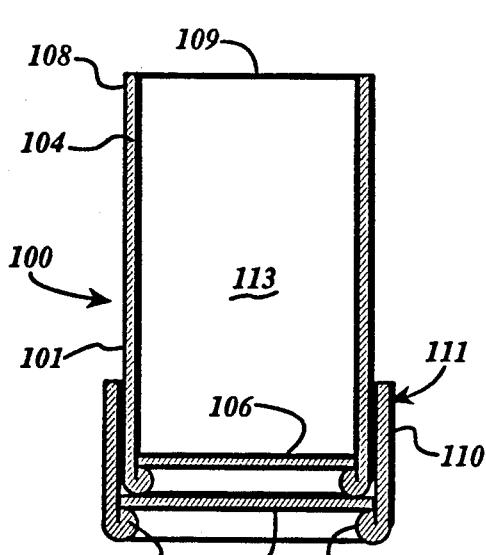
FIG. 10 is a side cross-sectional view of another embodiment of the system for collecting and disposing of medical wastes, having an open top, with the cover mounted for storage on the bottom.
Figure 11:
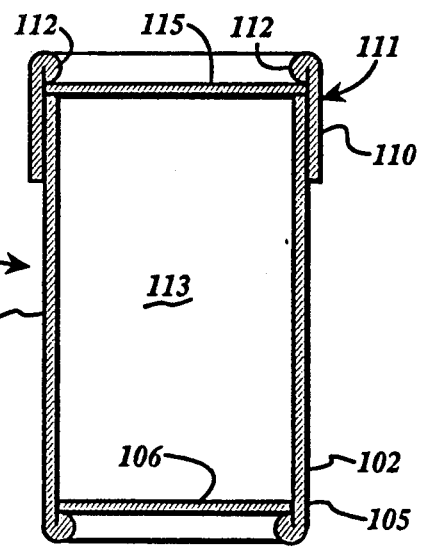
FIG. 11 is a side cross-sectional view of the embodiment of FIG. 10, with the cover closing the top opening.

FIGS. 10 and 11 illustrate an additional embodiment 100 of the system for collecting and disposing of medical wastes, which includes a cylindrical housing 101, with a lower cylindrical body 102 and an upper cylindrical body 104. The lower cylindrical body 102 is shown with a similar lower side wall 105 configuration as the lower cylindrical side walls of FIGS. 1-3 for supporting a circular seat 106. The upper cylindrical body 104 has an upper side wall 108 defining an opening 109 leading to a holding chamber 113 for receiving medical sharps and other medical wastes.

The housing 101 comprises a telescopic cover 110 with a cylindrical side wall 111 which is of sufficient internal breadth to telescopically fit tightly about the lower cylindrical body (FIG. 10) and the upper cylindrical body (FIG. 11). The telescopic cover 110 has on one end portion an inwardly projecting circular seat 112 which is attached to and supports a wall 115 for the telescopic cover.

FIG. 10 shows the telescopic cover 110 mounted about the lower cylindrical body 112 whereby the opening 109 is fully exposed to allow authorized medical personnel in operating rooms and emergency rooms to discard large volumes of hazardous medical wastes in a convenient manner. Additionally, the telescopic cover, when mounted in this position can serve as a base to stabilize the collector. In the medical environment, this configuration of the invention is most commonly referred to as a "kick bucket". FIG. 11 illustrates the telescopic cover 111 sealing the opening 109 of the kick bucket so as to provide a collector which securely contains the medical waste when transported from the operating room or the emergency room to the disposal site.

The preferred material of construction in all of the above embodiments comprises biodegradable, or otherwise known as non petroleum-based materials selected from the following group: natural cellulosic-based materials such as wood, cardboard, particle board and fiber board, non-natural cellulosic materials, such as rayon, cellophane, and cellulose-nitrate, and other materials, such as natural rubber and natural wax which when burned emit no more than trace amounts of sulphur or chlorine. These materials add to the Btu loading for completely rendering and transforming the contents of the collectors. Additional qualities which can be taken singly or in combination, are absorbency for absorbing liquids emitted from the medical wastes, leak resistance so as to avoid leaking liquid wastes, puncture resistance so as to avoid a needle of a syringe puncturing the wall of the collector, and rigidity so as to avoid inadvertent crushing.

Figure 12:
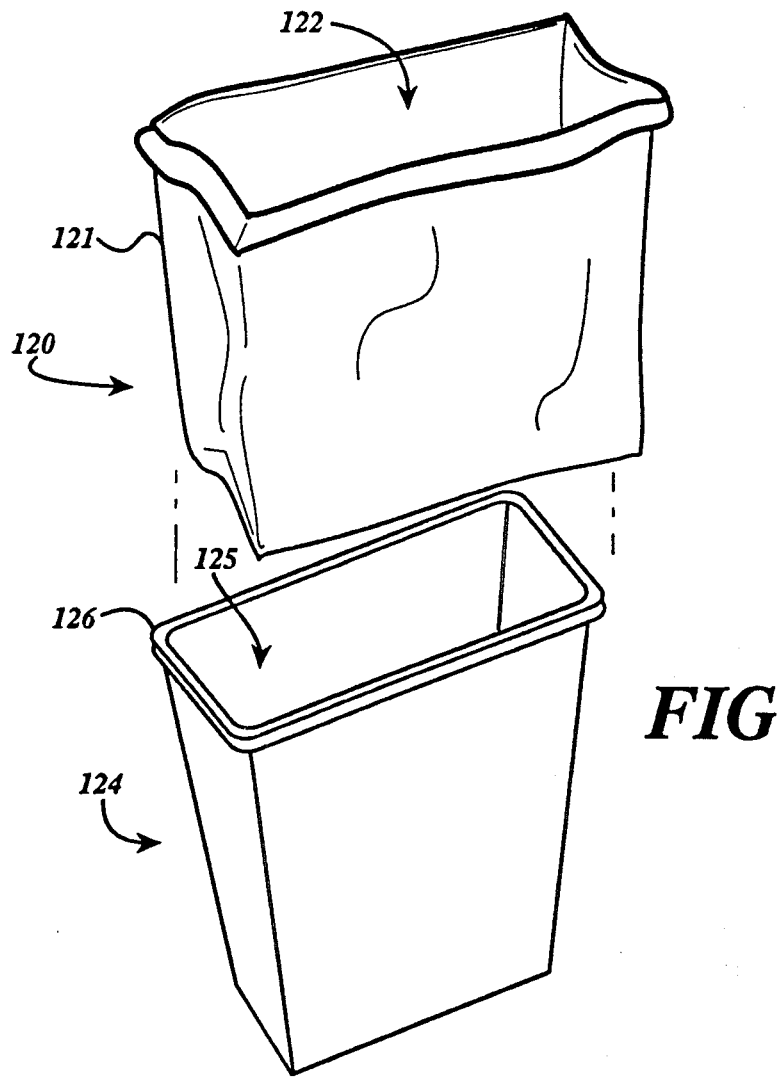
FIG. 12 is an exploded perspective view of another embodiment of the system for collecting and disposing of medical wastes.

FIG. 12 shows an additional embodiment 120 of the system for collecting and disposing of medical wastes including a receptacle 121 having an opening 122 therein, which takes the similar form and function of a generic trash bag. The receptacle 121 might be inserted into an opening 125 of any commercially available can or collector 124 or any of the above mentioned embodiments and can conform to the shape of its designated collector housing. The receptacle 121 will be of an appropriate size to function as a liner for the collector housing and leave a remaining flange about a rim 126 of the collector so as to hold itself in position and to ensure noncontamination of the rim of the collector.

The embodiment 120 can be formed of non-natural cellulosic materials, such as rayon, cellophane, and cellulose-nitrate, whereby when incinerated evolves no more than trace levels of sulfur or chlorine and yields substantially only biodegradable ash. Characteristics of this embodiment include leak-resistance, combustibility, and biodegradability, however, characteristics of this receptor do not necessarily include puncture-resistance and rigidity because of the general structure of the non-natural, cellulosic material. Thus, this embodiment is particularly advantageous for use when discarding chemotherapy, pathological, and other non-sharp medical wastes.

In some of the above described embodiments, the mass of the material used to form the housing is matched with the volume of the holding chamber which will receive a predetermined mass of syringes and other anticipated typical medical wastes so that the amount of the material of the housing is sufficient to emit enough heat when burned to transform the medical wastes in the holding chamber into a substantially noncontaminated and noncombustible residue or ash. After incineration of the collector housing, the ash of the collector itself will consist of a biodegradable "mineral" ash.

In some of the above described embodiments, geometric variations such as wall thickness and mass of the housing and the insert, can be adjusted relative to the internal collection volume of the holding chamber, to yield a predetermined ratio of the ash of the housing with respect to the ash of the medical waste, when incinerated. This ratio can be adjusted by increasing or decreasing the thickness of the collector walls so as to increase or decrease the weight of the collector, or by changing the size and/or shape of the collector without changing the weight of the collector.

Therefore, if it is desired that the ashes of incineration include more paper ash, which is biodegradable, and less plastic ash, which is not biodegradable, the manufacturer of the collector can adjust the size, volume and/or weight of the collector. Thus, the ash content can be adjusted so that the ash can be used, for example, as a fertilizer if it contains a high ratio of paper ash, or as an additive to a building material such as concrete or tar if it contains a high ratio of plastic ash.

EXAMPLE

For example when the empty collector is 250 mm high and 100 mm in inside diameter, the available volume is calculated: $h\pi r^2 = 1,963,494$ mm$^3$. If the syringe is 10 mm in outside diameter and 100 mm long, the occupied volume is calculated: $l\pi r^2 = 7,854$ mm$^3$. At 100% packing (theoretical case), 250 syringes fit into the collector's "occupied volume". For a practical case, the packing density is estimated at 25% of the theoretical full packing condition, which is 62 syringes. If each syringe weighs 0.75 ounces, there are 21.33 syringes per pound, so the loaded collector holds 2.93 pounds of syringes. If the empty collector comprises 8 ounces of cardboard, which yields 10% ash by weight, then upon burning the collector, the anticipated burn results of the collector are 0.05 pounds of ash. Assuming the syringes are plastic and yield 1.7% ash by weight, then upon burning, the anticipated burn results of 2.93 pounds of syringes yield 0.05 pounds of ash. Thus, upon burning the collector filled with a practical load of syringes the resulting ratio of plastic ash to paper ash is 1 to 1.

The wall thickness and other geometric variations of the collector housing can be tailored to accommodate the needs of different locations throughout the medical facility, and to accommodate different items to be deposited in the collectors and can be adapted relative to the collection volume within the housing to further control leak-resistance, puncture-resistance, incinerability, biodegradability, and other factors related to the system for collecting and disposing of medical wastes.

While this invention has been described in relation to these preferred embodiments, it will be apparent to those skilled in the art that the invention is susceptible to additional embodiments without departing from the spirit and scope of the invention. Therefore, it is intended that the invention not be limited except by the claims.

We claim:

1. A disposable collector for receiving and disposing of medical wastes, including syringes and scalpels and other forms of medical wastes needing incineration comprising:

a housing defining a holding chamber with an opening in communication with said holding chamber for the receipt of medical wastes, said housing being formed of a group of materials, selected from: natural cellulosic materials such as fiberboard, cardboard, molded cellulose, paper stock, wood, and particle board, non-natural cellulosic materials such as rayon, cellophane, and cellulosenitrate, and other materials such as natural rubber and natural wax which are combustible and biodegradable, and when burned evolve no more than trace levels of chlorine or sulphur and yields substantially only biodegradable ash, whereby when medical wastes are placed in the holding chamber and the housing is burned in a furnace the material of the collector burns and aids in the incineration of the medical wastes.

2. The collector of claim 1 and wherein the quantity of natural cellulosic, non-natural cellulosic, or other materials that form the housing is matched with the volume of the holding chamber which will receive a predetermined number of syringes and other anticipated typical medical wastes so that the material of the housing is sufficient to emit enough heat upon combustion to transform the medical wastes in the holding chamber into a substantially noncontaminated and noncombustible residue or ash.

3. The collector of claim 1 and wherein the housing is sufficiently rigid to hold its shape during initial combustion of the housing so as to retain the medical sharps in the holding chamber during initial combustion of the medical sharps.

4. The collector of claim 1 and wherein said material is liquid-absorptive so as to absorb any liquids that may be emitted from or residing on the medical wastes deposited in the holding chamber.

5. The collector of claim 1 and wherein the housing is sufficiently leak-resistant so as to safely contain the medical wastes, including liquid medical wastes which are deposited in the holding chamber.

6. The collector of claim 1 and wherein the housing is sufficiently puncture-resistant to accommodate the needs of different locations throughout the medical facility, and provide a safe medical environment for collecting and disposing of medical wastes.

7. The collector of claim 1 and further comprising a wall bracket including a support, ring, and wherein said collector housing is sized and shaped to be received in and supported by said support ring.

8. The disposable collector of claim 1 and wherein said housing is cylindrical and comprises a cylindrical side wall turned in at its ends to form inwardly projecting seats, and end walls at opposite ends of said housing supported by said seats.

9. The disposable collector of claim 8 and wherein said opening is formed in one of said end walls.

10. The disposable collector of claim 8 and wherein one of said end walls is scored to form weakened lines of separation, for permitting the medical wastes to open the scored portion of the end wall and be deposited inside the housing.

11. The disposable collector of claim 8 and wherein said housing comprises a telescopic housing structure, including a body and a telescoping cover mounted about said body, with the telescoping cover connected to said body.

12. The disposable collector of claim 1 and wherein said housing comprises two telescoping portions and an connection between said two telescoping portions.

13. The disposable collector of claim 12 and wherein the connection is made with adhesives which when burned emit no more than trace levels of chlorine or sulphur.

14. The disposable collector of claim 1 and further including a head with downwardly facing opening and a downwardly extending collar with a curved chute extending between said opening and said collar, said collar including support means for supporting the housing with the aperture of said housing mounted about said collar.

15. The disposable collector of claim 14 and wherein said collar of said head comprises studs which function as a connector and support means for mounting said collector to the head.

16. The disposable collector of claim 1 and wherein said housing is colored with coloring agents which are biodegradable.

17. The disposable collector of claim 1 and wherein said housing comprises a combination of tubes made of natural cellulosic material such as cardboard, fiberboard, particle board, paper stock, and wood, non-natural cellulosic materials such as rayon, cellophane, and cellulose-nitrate, and other materials such as natural rubber and natural wax which are combustible and biodegradable.

18. The disposable collector of claim 1 and wherein said housing material includes at least one of anti-microbial, anti-fungal, or anti-bacterial additives.

19. A disposable collector for medical wastes including medical sharps and other forms of medical wastes including chemotherapy wastes which require controlled incineration, comprising: a body defining a holding chamber formed of puncture and leak resistant, absorptive and combustible material, for absorbing fluids emitted from wastes placed in said body and for controlling combustion of said wastes, said combustible material being selected from a group of materials consisting of: natural cellulosic materials such as paper stock, cardboard, fiberboard, particle board, wood, and molded cellulose, non-natural cellulosic materials such as rayon, cellophane, and cellulose-nitrate, and other materials such as natural rubber and natural wax.

20. A disposable collector for receiving and disposing of medical wastes, including medical sharps and chemotherapy wastes, which require controlled incineration comprising:
a housing defining a holding chamber and an opening in communication with said holding chamber for the receipt of medical wastes,
an absorptive material in said holding chamber for absorbing any absorptive liquids emitted from the medical wastes, said absorptive material being selected from the group consisting of: natural cellulosic materials such as fiberboard, cardboard, molded cellulose, paper stock, wood, non-natural cellulosic materials such as rayon, cellophane, and cellulose-nitrate, and other materials such as natural rubber and natural wax,
said absorptive material comprising a combustible material which when burned emits no more than trace amounts of chlorine or sulphur and which aids in the burning of the medical wastes while the medical wastes are retained in the holding chamber.

21. The disposable collector of claim 20 and wherein said absorptive material is fabricated of the same but less dense material than the material of said housing.

22. A disposable collector for medical sharps including syringes and scalpels and other forms of medical wastes including chemotherapy wastes needing controlled incineration, comprising:
a housing formed of puncture and leak resistant combustible material, which when burned evolves no more than trace levels of chlorine or sulfur and which yields substantially only biodegradable ash upon combustion, and
an insert contained inside said housing of absorptive and combustible material for preferentially absorbing fluids emitted from wastes placed in said housing and for dispersing and thereby enhancing combustion of the fluids and medical wastes when burned.

23. The disposable collector of claim 22 and wherein said insert material includes at least one of anti-microbial, anti-bacterial, or anti-fungal additives.

24. The disposable collector of claim 22 and wherein said housing and said insert are fabricated of biodegradable material selected from the group consisting of: natural cellulosic materials such as paper stock, cardboard, fiberboard, particle board, and wood, non-natural cellulose materials such as rayon, cellophane and cellulose-nitrate, and other materials such as natural rubber and natural wax.

25. The disposable collector of claim 22 and wherein said absorptive material of said insert is selected from the group of materials consisting of: natural cellulosic materials such as fiberboard, cardboard, molded cellulose, paper stock, wood, and particle board, non-natural cellulosic materials such as rayon, cellophane, and cellulose-nitrate, and other materials such as natural rubber and natural wax,
said materials being of a density and configuration which provides increased absorption action for preferential absorption of liquid wastes.

26. The disposable collector of claim 22 and wherein said combustible material of said insert is selected from the group consisting of natural cellulosic materials such as paper stock, cardboard, fiberboard, particle board and wood, non-natural cellulose materials such as rayon, cellophane and cellulose-nitrate, and other materials such as natural rubber and natural wax, which provide enhanced combustion and aids in more complete combustion of the syringes and other forms of medical wastes in the holding chamber of the housing.

27. The disposable collector of claim 22 and wherein the mass of said insert can be adjusted by forming side walls of said insert with increased thickness.

28. The disposable collector of claim 22 and wherein said absorptive and combustible material of said insert consists essentially of cellulose.

29. The disposable collector of claim 22 and wherein said absorptive and combustible material of said insert consists essentially of paper pulp.

30. The disposable collector of claim 22 and wherein said housing and said insert are fabricated from a materials selected from a group of materials consisting of: natural cellulose materials such as paper stock, cardboard, fiberboard, wood, and particle board, non-natural cellulose materials such as rayon, cellophane, and cellulose-nitrate, and other materials such as natural rubber and natural wax and wherein the material of said insert is less dense than the material of said housing so as to provide preferential absorption and enhanced combustion relative to the material of said housing.

31. The disposable collector of claim 22 and wherein the material of said insert takes the shape of the housing.

32. The disposable collector of claim 22 and wherein the material of said insert comprises free particulate material.

33. The disposable collector of claim 22 and wherein said insert is fabricated of combustible material that burns at a faster rate than the material of said housing and upon combustion of said housing and said insert transforms the medical sharps and wastes contained in said housing into a substantially noncontaminated and noncombustible residue or ash.

34. A disposable collector for receiving and disposing of medical wastes including chemotherapy wastes needing incineration comprising:

a housing defining a holding chamber with an opening in communication with said holding chamber for the receipt of medical wastes, said housing being formed of material which is combustible, biodegradable, and when burned evolves no more than trace levels of chlorine or sulphur and yields substantially only biodegradable ash, whereby when chemotherapy wastes are placed in the holding chamber and the housing and aids in the incineration of the chemotherapy wastes.

* * * * *